(12) United States Patent
Weiss et al.

(10) Patent No.: US 8,440,462 B2
(45) Date of Patent: May 14, 2013

(54) USE OF A HYDROGEL FOR THE CULTURE OF CHONDROCYTES

(75) Inventors: Pierre Weiss, Saint Herblain (FR); Jérôme Guicheux, Nantes (FR); Guy Daculsi, Vigneux de Bretagne (FR); Gaël Grimandi, Nantes (FR); Claire Vinatier, Nantes (FR)

(73) Assignees: Institut National de la Sante et de la Recherche Medicale (INSERM), Paris (FR); Universite de Nantes, Nantes (FR)

( * ) Notice: Subject to any disclaimer, the term of this patent is extended or adjusted under 35 U.S.C. 154(b) by 70 days.

(21) Appl. No.: 12/785,874

(22) Filed: May 24, 2010

(65) Prior Publication Data

US 2010/0297764 A1    Nov. 25, 2010

Related U.S. Application Data

(62) Division of application No. 10/577,942, filed as application No. PCT/FR2004/002844 on Nov. 4, 2004, now abandoned.

(30) Foreign Application Priority Data

Nov. 4, 2003  (EP) .................................. 03292759

(51) Int. Cl.
*C12N 5/00*    (2006.01)

(52) U.S. Cl.
USPC ........................... 435/395; 435/374; 435/377

(58) Field of Classification Search .................. 435/395, 435/374, 377
See application file for complete search history.

(56) References Cited

U.S. PATENT DOCUMENTS

| 5,709,854 | A | * | 1/1998 | Griffith-Cima et al. | ....... 424/426 |
| 5,902,741 | A | * | 5/1999 | Purchio et al. | ................ 435/325 |
| 6,001,394 | A | * | 12/1999 | Daculsi et al. | ................ 424/489 |
| 6,365,405 | B1 | * | 4/2002 | Salzmann et al. | ............ 435/366 |

FOREIGN PATENT DOCUMENTS

WO    WO 9705911 A1 *  2/1997

OTHER PUBLICATIONS

Turczyn et al. J. Biomater. Sci., Polymer Edn. (2000) 11(2): 217-223.*
Merceron et al. Bio-Medical Materials Eng. (2010) 20: 159-166.*

* cited by examiner

*Primary Examiner* — Susan Hanley
(74) *Attorney, Agent, or Firm* — B. Aaron Schulman, Esq.; Stites & Harbison, PLLC (57) ABSTRACT

The invention relates to the use of a silanised hydroxypropylmethylcellulose (HPMC) or silanised hydroxyethylcellulose (HEC) hydrogel, self-crosslinking as a function of pH, for the three-dimensional ex vivo culture of chondrocytes.

16 Claims, 2 Drawing Sheets

USE OF A HYDROGEL FOR THE CULTURE OF CHONDROCYTES

This application is a divisional application of U.S. application Ser. No. 10/577,942, filed Dec. 18, 2006 now abandoned, which is a National Stage Application of PCT/FR04/002844, filed Nov. 4, 2004.

The invention relates to the use of a cellulose hydrogel for the three-dimensional culture of chondrocytes, for the implantation thereof in a cartilaginous site.

Cartilage is a specialized non-vascularized, non-innervated strong and resilient connective support tissue. It is present in the ribs, the sternum, the nose and ears, but also in the joints. Cartilage contains specialized cells known as chondrocytes and an extracellular matrix (ECM) basically consisting of collagen fibers and proteoglycans.

The articular cartilage may be the seat of numerous changes of inflammatory origin (rheumatoid arthritis, osteoarthritis), of traumatological origin or related to ageing (arthrosis). The establishment of these cartilage pathologies results, over the more or less long term, in degradation of the extracellular matrix and a decrease in cellularity. The absence of vascularization and chondrocyte proliferation imparts to this tissue low repair capacities, which render these catabolic processes irreversible. In view of population ageing, these degenerative pathologies now affect a significant proportion of the population and are therefore a major public health issue. In this context, the scientific community has for a number of years been interested in means for regenerating a functional cartilaginous tissue.

Abrasive chondroplasty, microfracture or spongialization surgical techniques have been proposed in order to stimulate the poor spontaneous repair properties of the cartilage (Hunziker, 2002). These techniques, which allow the formation of a blood clot of subchondral origin, result in the formation of a cartilaginous tissue which remains fibrous and transient (Shapiro et al., 1993). At the same time, techniques for the transplantation of tissue having chondrogenic properties have also been studied. The use of periosteal or perichondrial autologous transplants and of osteochondral tissues (mosaicplasty) has allowed the neoformation of a cartilaginous-type tissue after implantation (Hunziker, 2002). The numerous limitations of these techniques (instability of the graft, calcification, low reproducibility of the clinical results) and the restriction of their indication to the repair of focal lesions, have recently led to the development of new tissue engineering techniques which are applied to traumatological pathologies of the cartilage.

Brittberg et al. were the first to propose a repair method based on the transplantation of autologous chondrocytes (Brittberg et al., 1994). This method takes place over three stages: firstly, a cartilage fragment is removed from a non-load-bearing zone in order to isolate chondrocytes, which are then multiplied in vitro as a monolayer, then reimplanted below a periosteal flap of the lesion. The results revealed repair of the cartilaginous defect, but the patients have to undergo two intensive surgical procedures. Furthermore, the phenotype of the cells after the monolayer amplification thereof still has to be determined.

A plurality of three-dimensional matrices of plant or animal origin, such as collagen sponges, fibrin, hyaluronic acid or alginate, have also been developed (Cancedda et al., 2003). The risk of virus transmission associated with the use of these biological materials and the inflammatory reactions observed during pre-clinical tests have led current research toward the development of entirely synthetic biomaterials (Hunziker, 2002). Polymers, such as polylactic acid, polyglycolic acid, carbon fibers, polyester urethane, Dacron and Teflon, have been proposed and used in vitro for the 3D culture of chondrocytes or mesenchyme cells. Some of these synthetic polymers have caused immune responses or inflammation after the implantation thereof in a cartilaginous site (Cancedda et al., 2003).

Injectable hydrogel compositions are described, in particular, in U.S. Pat. No. 6,129,761.

The inventors have now demonstrated the benefit, for implantation in a cartilaginous site, of the three-dimensional cultivation of chondrocytes within a hydrogel self-crosslinking as a function of pH.

The hydrogel used is a hydrogel which self-crosslinks as a function of pH and consists of an aqueous hydroxyethylcellulose (HEC) or hydroxypropylmethylcellulose (HPMC) solution onto which are grafted silane groups which allow the formation of covalent bonds between the HEC or HPMC chains.

This type of polymer material is described in association with an inorganic filler in international patent application WO 97/05911.

This material preferably consists of a polymer of simplified formula:

(HEC or HPMC)—O—X—Si(OZ)$_3$ which may be obtained by the reaction of hydroxyethylcellulose (HEC) or hydroxypropylmethylcellulose with a compound of formula (1):

$$XSi(OZ)_3 \quad (1)$$

wherein X represents a halogen atom or a hydrocarbon group having an epoxy function, in particular $C_{2-20}$, and Z is selected from among a hydrogen atom, an alkali metal and an alkyl group, in particular $C_{1-5}$.

The compound of formula (1) may be, for example, (3-glycidoxypropyl)trimethoxysilane:

In a basic medium, the organosilicon compound grafts onto the HEC or the HPMC, opening the epoxide, and the methoxysilane groups are hydrolyzed to produce a polymer of simplified formula:

(HEC or HPMC)—O—CH$_2$—CH—OH—CH$_2$O—(CH$_2$)$_3$—Si—(O$^-$Na$^+$)$_3$.

The polymer is preferably a silanized HPMC polymer.

This polymer is stable in aqueous solution at a pH greater than or equal to approximately 12.4. Acidification of the solution causes a gradual increase in viscosity and the formation of a hydrogel. This physical phenomenon corresponds to the crosslinking of the polymer by (i) transformation of the silanolate groups into silanol groups:

∼SiO—Na$^+$ → ∼SiOH then formation of a three-dimensional network by (ii) condensation of one silanol on another silanol:

and/or
(iii) condensation of a silanol on a hydroxyl group of the cycles of the cellulose ethers or the substituents:

This covalent-type crosslinking, caused by a reduction in the pH of the aqueous solution of the polymer, is reversible and the hydrogel redissolves when the pH of the medium is increased. Thus, before it is used, the synthesized polymer may be in the form of a powder which may be dissolved in an alkaline sodium hydroxide solution. The gelation pH is between 7 and 12, depending on the desired crosslinking rate.

The gel obtained may be sterilized by autoclaving (for example, at 121° C. for 20 minutes).

The polymer in basic aqueous solution, before crosslinking, may also be mixed, prior to its biological use, with a physiological buffer solution. The pH of the final mixture is thus adapted to the desired handling time prior to crosslinking of the overall mixture. This crosslinking time may be measured by oscillatory rheometry and may vary from 5 minutes to 5 days as a function of the parameters of this mixture—mainly the pH and the temperature (Bourges et al., 2002a; Bourges et al., 2002b).

In order to provide a suitable crosslinking rate for the intended application, it is desirable that the side silicon carrier groups, of the silanolate or alkali metal or ammonium silanolate precursor type, represent from 0.5 to 5% of the total dry weight of the polymer.

The invention relates to the use of a silanized HEC or silanized HPMC hydrogel of this type, self-crosslinking as a function of pH, for the three-dimensional ex vivo culture of chondrocytes.

The hydrogel used has, in particular, the following advantages:
  it is biocompatible with chondrocyte cells integrated within it;
  the chondrocytes are intimately integrated in the hydrogel;
  the chondrocytes dedifferentiated by monolayer amplification redifferentiate within the hydrogel and maintain chondrocyte characteristics;
  the crosslinking is controllable by the pH of the biological buffer added to the mixture of hydrogel and chondrocyte cells.

The cells cultured in the hydrogel are preferably human or animal chondrocytes, preferably autologous chondrocytes, of patients having a lesion of the cartilage. These cells may, for example, be removed from a cartilaginous tissue, for example from a portion of the articular cartilage or from the nasal cartilage.

The cells cultured in the hydrogel may also be undifferentiated cells capable of chondrogenic differentiation. Mesenchymate stem cells or stem cells originating from fatty tissue are thus included. The former may, in particular, be obtained by removing bone marrow (typically by suction, using a syringe, from the trabecular bones such as long bones, iliac crest), the latter by liposuction (typically by suction under vacuum of fatty masses).

These undifferentiated cells are then cultivated in the presence of the hydrogel under conditions allowing the induction of a chondrocyte phenotype. These conditions are preferably a culture in conventional culture media (DMEM or MEM), to which are added glutamine and antibiotics, if required, and, preferably autologous, animal or human serum, or serum substitutes, and also chondrogenic additives. Examples include, in particular, insulin, transferrin, sodium selenite, ascorbic acid, TGF-beta, IGF-1, BMP (bone morphogenetic protein), dexamethasone, linoleic acid, BSA (bovine serum albumin) or pyruvate. Other additives may also be used in order to induce the chondrogenic differentiation of the cells. The culture is preferably produced under moist conditions at 37° C. in the presence of oxygen concentrations which may vary as required. Hypoxia has been found to be an important factor for the development of a chondrocyte phenotype.

The invention also relates to an ex vivo process for the preparation of a complex of cells integrated in a hydrogel, the complex being intended to be injected into a cartilaginous site, wherein said process includes the ex vivo mixing of chondrocytes or of undifferentiated cells, capable of chondrogenic differentiation with a silanized HEC or HPMC hydrogel, crosslinking as a function of pH, in a biological buffer at an appropriate pH for the crosslinking of the hydrogel, under appropriate conditions and for an appropriate period for the integration and the three-dimensional culture of the chondrocytes, optionally derived from the differentiation of said undifferentiated cells, in the hydrogel.

A person skilled in the art may use any biological buffer. Examples include the phosphate buffer (PBS, phosphate buffered saline), HEPES or TRIS buffer. Any biological medium known to a person skilled in the art, for example DMEM medium or alpha-MEM medium (alpha minimum essential medium), may also be used.

Preferably, the process includes the following ex vivo steps:
  the monolayer amplification of chondrocytes on a solid support, such as a culture plate;
  the harvesting of the amplified chondrocytes, dedifferentiated through the monolayer amplification thereof;
  the mixing of the dedifferentiated amplified chondrocytes with the hydrogel in a biological buffer at an appropriate pH for the crosslinking of the hydrogel, resulting in the integration of the chondrocytes within the hydrogel and in the redifferentiation thereof.

The rheological properties of the hydrogel consisting of silanized HEC or HPMC allow it to be injected at the implantation site, thus promoting the vectorization of the chondrocytes by non-invasive surgery.

The hydrogel within which the chondrocytes were cultivated may be implanted in a site of the lesion normally occupied by cartilage.

The targeted lesions may be losses of focal cartilaginous substances related to traumatological sequelae or, more generally, any osteoarticular or plastic cartilaginous pathologies or losses.

The invention may be applied to the engineering of all of the cartilaginous tissues, i.e. of the following types:
  hyaline (present in the nasal septum, the larynx, the tracheal rings, the articulations or at the sternal end of the ribs);
  fibrocartilage (present in the intervertebral discs, specific articular cartilages, and the pubic symphysis);
  resilient (present in the auricle, the external auditory canal, the epiglottis, the eustachian tube, and the laryngeal cartilages).

Repair of the intervertebral discs is particularly desired. The cause of lumbago is not known but might be due to the intervertebral disc and the inevitable and age-related deterioration thereof. The intervertebral disc is a fibrocartilaginous structure consisting of four concentric tissues disposed between the adjacent vertebral bodies. The outer layer is the outer fibrous ring, which consists of markedly oriented collagen fibers. The inner fibrous ring has a lower collagen density and is less organized than the outer ring. The transition zone is a thin zone of fibrous tissue separating the inner ring from the nucleus pulposus, a gelatinous central zone forming a nucleus. The intervertebral discs are hypovascularized and have limited innervation. In adults, the discs are fed by the diffusion of nutriments and metabolites. The discs contain relatively few cells embedded in an abundant extracellular matrix consisting mainly of water, proteoglycans, collagen and non-collagenic proteins. The cells of the disc synthesize these macromolecules and maintain and repair this extracellular matrix. In adults, the chondrocyte cells are the only cells of the nucleus. The inner fibrous ring, the transition zone and the cartilaginous plate of the adjacent vertebral bodies also contain chondrocytes, whereas the outer ring contains mostly fibroblast-type cells. A specific degree of disc degeneration occurs in all individuals. A clear association has been revealed between the age and the degeneration of the discs. Degeneration has been observed from the second decade of life onward. Persons having symptomatic discs experience acceleration of the normal ageing process, owing to both acquired and genetic factors.

The invention therefore also relates to a process for the treatment of the human or animal body, including the administration by injection of hydrogel, as defined above and previously colonized ex vivo by chondrocytes, for example using the process as described above.

The injection may be carried out using a system comprising a sterilizable syringe and connection pieces provided with single-use plungers, for example the system sold by HAWE NEOS DENTAL, comprising a syringe sterilized by autoclaving (ref. No. 440, Syringe Hawe-Centrix C-R$^R$, Mark III) and connection pieces (ref. No. 445).

The following figures and examples illustrate the invention without thereby limiting its scope.

EXAMPLES

Example 1

Preparation of the Hydrogel

Materials:
HPMC E4M® (Colorcon—Dow Chemical, France)
Glycidoxypropyltrimethoxysilane (GPTMS) (Acros, Belgium)
HEPES (Sigma-Aldrich, St Louis, USA)
NaOH (VWR International, Fontenay-sous-Bois, France)
NaCl (VWR International)
HCl 0.1 M (Sigma Aldrich).

Foetal calf serum (FCS) (Dominique Dutscher, Brumath, France).

a) Synthesis of Silanized Hydroxypropylmethylcellulose (Si—HPMC) Powder

The syntheses were carried out on quantities of 240 grams of HPMC. The selected polysaccharide was E4M®. The synthesis was carried out using glycidoxypropyltrimethoxysilane (GPTMS) in a 6-liter flask in a heterogeneous medium in an organic solvent (Bourges et al., 2002). The synthesis was carried out while boiling for 3 hours. The silanized HPMC powder was firstly oven-dried for 1 night, then lyophilized (Christ Alpha 1-4 ST).

b) Preparation of Silanized Hydroxypropylmethylcellulose Solution 6 grams of Si—HPMC powder were solubilized in 200 ml of a 0.2 M NaOH solution. This mixture was stirred for 48 hours. The Si—HPMC solution was then dialyzed for 16 hours in a 0.09 M NaOH solution. A second dialysis was then carried out in a 0.09 M NaOH solution for 2 hours. This 3% Si—HPMC solution was then aliquoted and steam-sterilized (121° C., 30 minutes).

c) Induction of Crosslinking of the Hydrogel

The hydrogel used for the cell culture was prepared extemporaneously by mixing, under a laminar flow hood, 7.5 ml of Si—HPMC solution with 7.5 ml of HEPES buffer, with 10% of FCS being added. The HEPES buffer was prepared by dissolving 3.1 g of HEPES and 0.8 g of NaCl in a 0.03 M HCl solution. This solution was then aliquoted and steam-sterilized (121° C., 30 minutes).

This HEPES/Si—HPMC mixture was vortex-stirred for 15 seconds, then centrifuged at 1200 rpm for 2 minutes. This mixture was transferred to the culture plate. The culture medium was added 1 hour later.

d) Physical Characterization of the Hydrogel by Rheology

Equipment and methods

In order to characterize the crosslinking of the hyrogel, the inventors measured two rheological parameters: the dispersive module G" (characteristic of the liquids) and the conservative module G' (characteristic of the solids). This measurement was carried out using a rheometer (Rhéostress 300, Thermo Haake, Karlsruhe, Germany) provided with a planar cone having a diameter of 60 mm and an angle of 1° (C60/1 titan, planar cone, Thermo Haake). The gap between the truncation and the plate was 0.053 mm. The measurement was carried out in oscillatory mode with 3 oscillation frequencies (1 Hz, 3.2 Hz and 10 Hz) and an imposed stress of 1 pascal, at a temperature of 37° C. and for 1,200,000 seconds (13.8 days). The results are expressed in Pa.

Results

The hydrogel has the characteristics of a viscous liquid during the preparation thereof. During its crosslinking, its physical characteristics develop toward those of a gel. The hydrogel prepared according to the preferred embodiment, presented in Example 1, consists, once the crosslinking process has been completed (10 days), of 1.5% of dry polymer and 98.5% of water—a water content comparable to that of cartilage. The calculated mesh size of the hydrogel (0.22 µm) appears to be less than the size of a cell.

In order to establish the physical characteristics of the hydrogel, such as the gel point corresponding to the start of the crosslinking process, the crosslinking time and the mesh size of the hydrogel, the development, as a function of time, of the liquid component (G") and the resilient component (G')

was measured for three different frequencies. A pair G'/G" therefore corresponds to each frequency. The Tan Δ of each pair was traced, these three curves meeting at one point: the gel point. The crosslinking of the hydrogel started 33 minutes after the preparation thereof and was completed 244 hours (10 days) later—the moment at which the resilient component (G') plateaus at a value of 310 Pa. This value of the resilient component allowed us to calculate the mesh size of the hydrogel.

$$\xi = \left(\frac{KT}{G'}\right)^{1/3}$$
$$= \left(\frac{1.38 \times 10^{-23} \times 300}{310}\right)^{1/3}$$
$$= \left(\frac{4.14 \times 10^{-21}}{310}\right)$$
$$= 23.7 \text{ nanometers}$$

Under the preparation conditions described above, the average statistical mesh size of the hydrogel (Xi) was 0.023 µm.

TABLE 1

Results of the rheological characterization of 3% Si-HPMC hydrogel

| Vol. Si-HPMC solution | Vol. buffer | % Si-HPMC | Final % of Si-HPMC | pH mixture | G' | KT/G' | Xi (ξ) in micrometers | Gel point in minutes |
|---|---|---|---|---|---|---|---|---|
| 1 | 1 | 3.00% | 1.50% | 7.37 | 310 | 1.3355E−23 | 0.023 | 33 |

Example 2

Cytotoxicity Test of the Hydrogel

Materials and Methods 2.1 Cell Culture
a) Chondrocyte Lines
Materials:
Dulbecco's modified Eagle medium (DMEM) (Invitrogen corporation, Paisley, UK).
Ham's F12 nutrient medium (Invitrogen corporation).
Penicillin/streptomycin (Invitrogen corporation)
L-glutamine (Invitrogen corporation)
Trypsin/EDTA (Invitrogen corporation).

The inventors used the human chondrocyte lines SW1353 and C28/I2, derived from a human chondrosarcoma (Mengshol et al., 2000) and from human costal cartilage immortalized by the T antigen of the simian virus 40 (Goldring et al., 1994). These cells were cultivated in a DMEM and Ham's F12 volume/volume mixture, to which were added 10% of FCS, 1% of penicillin/streptomycin and 1% of L-glutamine (complete DMEM/F 12), under a moist atmosphere at 37° C. and containing 5% $CO_2$.

The culture medium was renewed in its entirety every other day. Once the cells had reached 80 to 90% of the confluence, they were treated with 2 ml of trypsin (0.025%)/EDTA (0.01%). Following incubation for 3 minutes at 37° C., the trypsin/EDTA solution was collected and centrifuged (8 min, 1200 rpm) in the presence of 8 ml of complete DMEM/F12 medium. Following elimination of the supernatant, the cell pellet was reconstituted with 10 ml of complete DMEM/F12. The cells were then counted and distributed over 25 $cm^2$ flasks having a density of 10,000 cells/$cm^2$.

b) Primary Chondrocytes
Isolation of human nasal chondrocytes
Materials:
Hank's balanced salt (HBSS, Invitrogen Corporation).
Protease (Pronase, Sigma-Aldrich).
Type IV collagenase (Sigma-Aldrich).

Human nasal cartilage was removed, having obtained the informed consent of patients undergoing reconstructive rhinoplasty. The nasal cartilage was washed five times in Hank's balanced salts (HBSS) and cut up into chips under a laminar flow hood. The cartilage chips were then incubated for 30 minutes at 37° C. in HBSS containing 1 mg/ml of protease. The chips were then rinsed three times in HBSS, then incubated for 4 hours, with stirring, in complete DMEM (10% FCS, 1% penicillin/streptomycin and 1% L-glutamine) containing 0.625 mg/ml of collagenase. The supernatant was centrifuged for 5 minutes at 1400 rpm. The pellet was washed once in HBSS, centrifuged (8 min, 1200 rpm) and re-suspended in 10 ml of complete DMEM. The cells were counted and transferred into a 25 $cm^2$ flask with a cell density of 10,000 cells/$cm^2$. The cells were cultured in a moist atmosphere at 37° C. with 5% $CO_2$. The culture media were renewed every other day. Once the cells had reached 80 to 90% confluence, they were treated using trypsin/EDTA as described above.

Isolation of rabbit articular chondrocytes
Materials:
Hyaluronidase (Sigma-Aldrich).
Trypsin (Sigma-Aldrich).
*Clostridium histolyticum* type II collagenase (290 U/mg, Sigma-Aldrich)
Cell screen (Falcon, Franklin Lakes, USA).

As previously described by Ghayor et al., 2000, newly born rabbits, aged 12 or 13 days, were slaughtered by cervical dislocation following anesthesia. Under a laminar flow hood, the front and rear paws were removed and stripped of their soft tissue. The knee and shoulder joints were then dislocated. The articular cartilage was cut into fine slices using a scalpel, and the chips obtained were placed in HBSS. These chips were incubated firstly for 10 minutes at 37° C. in 12 ml of HBSS containing 0.05% of hyaluronidase, then for 15 minutes at 37° C. in 6 ml of HBSS containing 0.2% of trypsin. After 2 rinsings in HBSS, the chips were transferred into HBSS containing 0.2% of collagenase and incubated for 30 minutes at 37° C.

The chips underwent a final step of digestion by incubation for 15 hours in a complete DMEM solution enriched with 0.03% of collagenase. The digestion product was filtered through a cell screen, collected and centrifuged (8 min, 1200 rpm). The cell pellet was re-suspended in 20 ml of complete DMEM. The cells were counted and transferred into a 25 $cm^2$ flask with a cell density of 10,000 cells/$cm^2$. Finally, the cells were cultured in a moist atmosphere at 37° C. with 5% $CO_2$.

The culture media were renewed every other day. Once the cells had reached 80 to 90% of the confluence, they were treated with trypsin/EDTA as described above.

2.2. Study of the Cytotoxicity of the Hydrogel a) Experimental Conditions

Materials:

Corning-Costar 24-well culture plate (Corning BV, Schiphol-Rijk, The Netherlands).

Actinomycin D (Sigma-Aldrich)

DMSO (Sigma-Aldrich)

Methyl tetrazolium salt (MTS) (Cell Titer 96 MTS, Promega Corporation, Madison, Wis.).

Phenyl methyl sulfoxide (PMS) (Sigma-Aldrich).

Phosphate buffered saline (PBS, Invitrogen Corporation)

In order to determine the cytotoxicity of the hydrogel, the human primary chondrocytes, the SW1353 and C28/I2 cells, were distributed over 24-well culture plates with a density of 10,000 cells per $cm^2$. After 24 hours of incubation at 37° C. in an atmosphere containing 5% $CO_2$, the cells were cultivated in the presence (500 µl of Si HPMC per well) or in the absence (500 µl of complete medium) of hydrogel for 24, 48 and 72 hours. Cells cultivated in the absence of hydrogel were also treated with actinomycin D (5 µg/ml) or the excipient thereof (DMSO) to provide a positive cytotoxicity control.

b) MTS Test

This colorimetric test measures the capacity of the mitochondria of the living cells to oxidize the tetrazolium salt MTS in formazan. The colored product formed is proportional to the dehydrogenase activity of the mitochondria. The absorbance measurement therefore allows the cell viability to be quantified. After 24, 48 and 72 hours of incubation under the conditions described above, the cells were washed with complete medium and incubated for 1 hour at 37° C. in the presence of 100 µl of MTS reagent containing 48 µg/ml of PMS and 2 mg/ml of MTS. The absorbance measurement at 490 nm was carried out by a microplate reader (MRX, Dynatech Laboratories, VWR International). The results are expressed as a percentage of MTS activity relative to the control conditions (cells cultivated in the absence of hydrogel).

c) Cell Count

After 24, 48 and 72 hours of incubation under the conditions specified above, the culture medium with or without hydrogel was drawn up and replaced by 200 µl of trypsin/EDTA. The cells were incubated for 2 minutes in a moist atmosphere at 37° C. containing 5% $CO_2$. The cells were then collected and centrifuged (8 min, 1200 rpm) in the presence of 2 ml of complete culture medium. The pellet was resuspended in 2 ml of complete culture medium and the cells were counted after vital staining with a trypan blue solution (0.04% in PBS) on a Malassez cell. The results are expressed in the total number of cells per well.

Results 2.3 Characterization of the Human Nasal Chondrocytes

In order to characterize the phenotype of the isolated human nasal cartilage cells, the inventors studied by RT/PCR the expression of specific markers of the chondrocyte phenotype after isolation and during a monolayer culture. This study revealed that the freshly isolated nasal chondrocytes (P0) expressed collagen II, aggrecan and collagen X, but also collagen I. During the various passes, the inventors observed a modification of the expression of these various genes. The expression of type II collagen decreased between P0 and P3. The expression of aggrecan dropped between P0 and P1. Collagen X was slightly expressed by the freshly isolated chondrocytes, its expression was no longer detectable at P3. The expression of type I collagen, conversely, increased markedly between P2 and P3.

These results revealed that the freshly isolated nasal chondrocytes expressed collagen II, aggrecan and collagen X. The expression of these chondrocytes markers decreased in monolayer culture and was associated with a marked increase in the expression of type I collagen.

2.4 Cytotoxicity of the Hydrogel a) Measurement of the MTS Activity of the Chondrocytes Cultivated on Contact with the Gel:

In order to determine the cytotoxic effect of the hydrogel on the chondrocytes, the inventors analyzed the MTS activity on the SW1353 and C28/I2 cell lines and on the human nasal chondrocytes after 24 hours, 48 hours and 72 hours of culture in contact with the Si—HPMC hydrogel.

Figure 1:
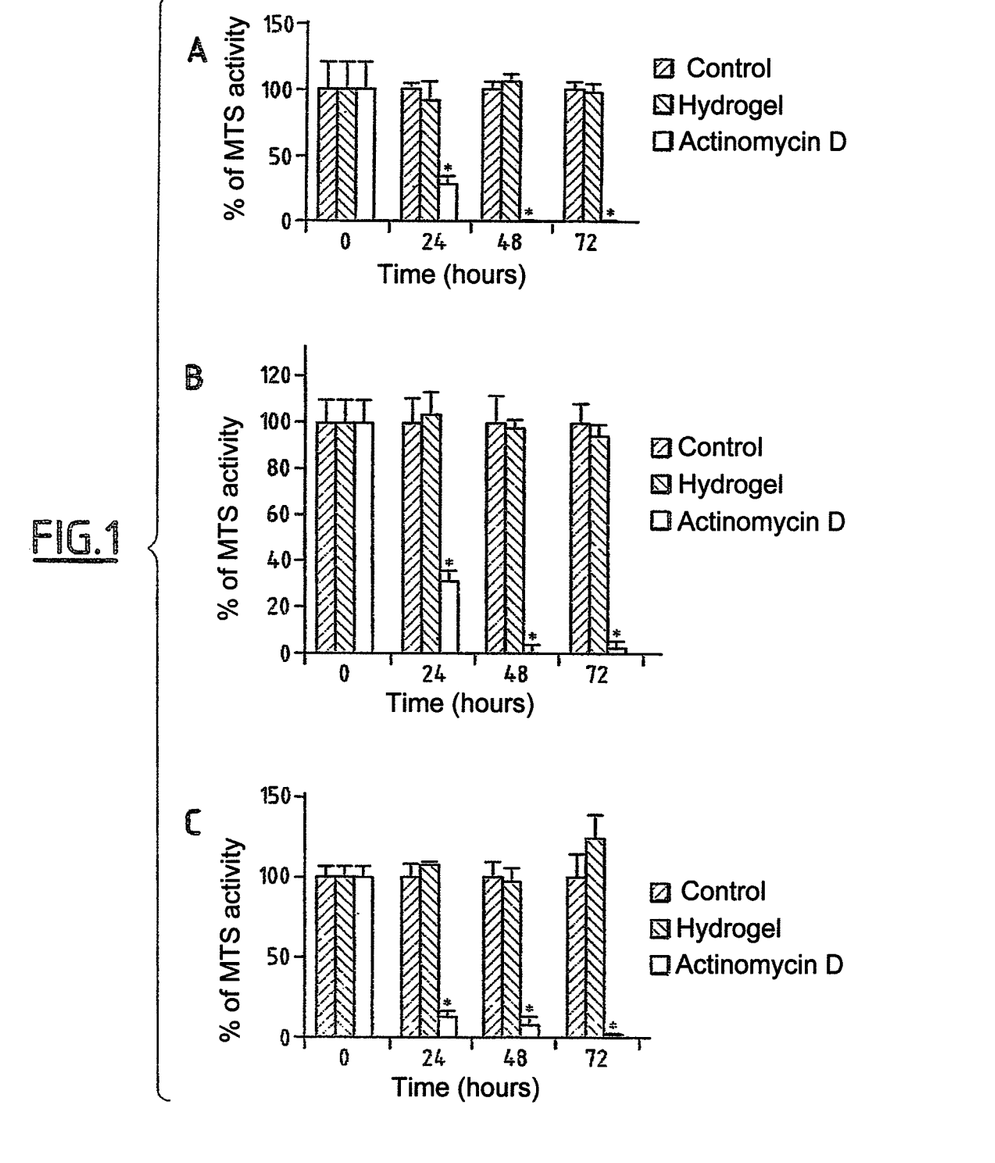
FIG. 1A to 1C illustrate the MTS activity of the chondrocytes cultivated for 24, 48 and 72 hours under control conditions (absence of hydrogel), in contact with the si-HPMC hydrogel, or in the presence of actinomycin D (5 µg/ml). SW1353 (FIG. 1A), C28/I2 (FIG. 1B) and human nasal chondrocytes (FIG. 1C). *p<0.001 compared to the control at each stage.

The results revealed that MTS activity was not modified by the presence of the hydrogel: no significant difference was observed, for the SW1353, C28/I2 chondrocytes and the human nasal chondrocytes, between the control culture conditions and the culture produced on contact with the hydrogel. Actinomycin D, on the other hand, a transcription inhibitor used in this case as a positive cytotoxicity control, caused a significant decrease in MTS activity from 24 hours onward. After 24 hours in the presence of actinomycin D, the MTS activity of the SW1353 and C28/I2 chondrocytes and those isolated from human nasal cartilage had decreased by 72%, 69% and 86% respectively (FIG. 1A to 1C).

Figure 2:
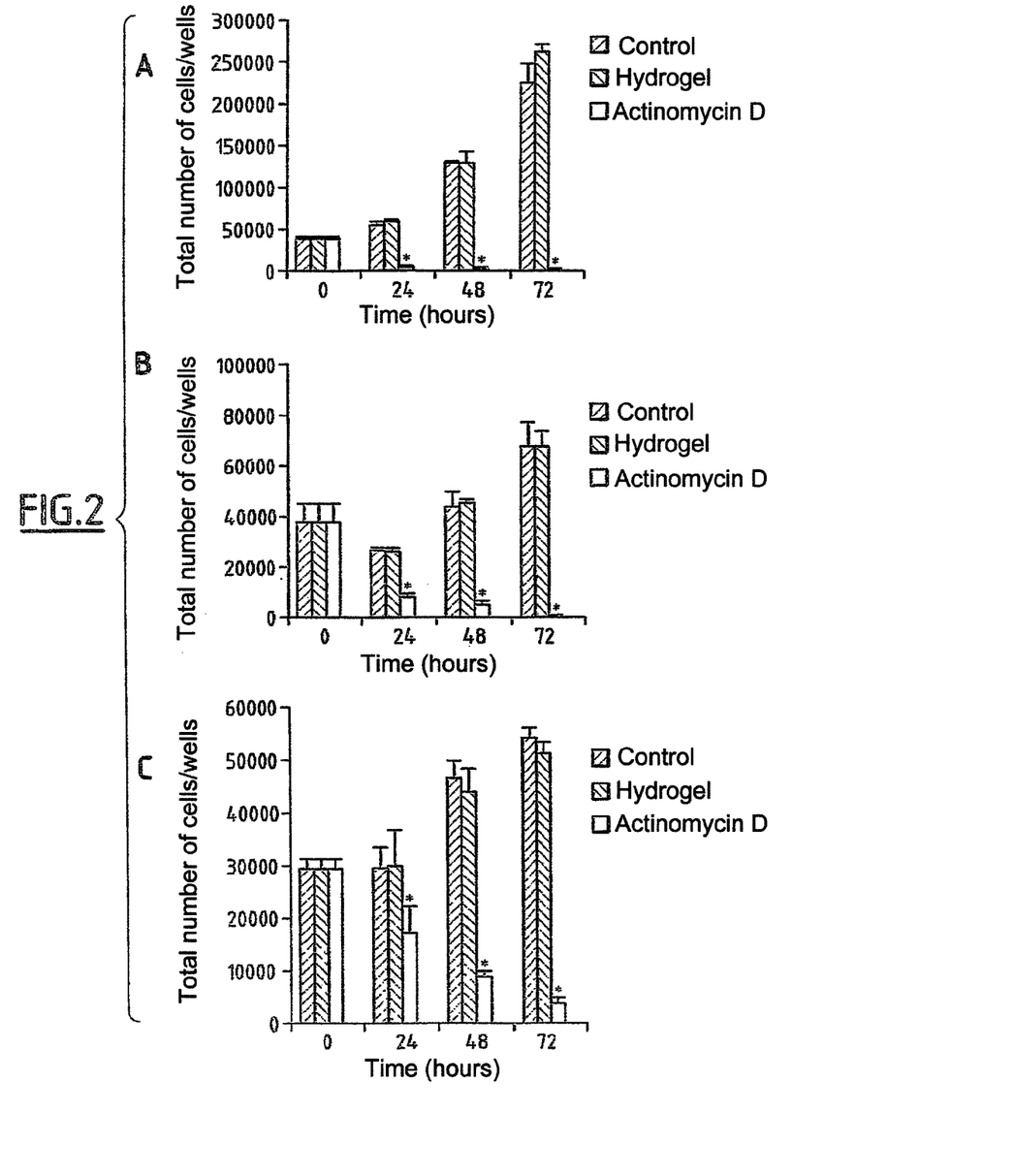
FIG. 2A to 2C illustrate the count of the chondrocytes cultivated for 24, 48 and 72 hours under control conditions (absence of hydrogel), in contact with the si-HPMC hydrogel, or in the presence of actinomycin D (5 µg/ml). SW1353 (FIG. 2A), C28/I2 (FIG. 2B) and human nasal chondrocytes (FIG. 2C). *p<0.001 compared to the control at each stage.

These results revealed that the hydrogel had not affected the MTS activity of the SW1353 and C28/I2 chondrocytes, nor that of the human nasal chondrocytes.

b) Trypan Blue Count:

In order to determine the influence of the hydrogel on cell proliferation, the inventors carried out a cell count by means of trypan blue staining. This staining allowed the living cells (white) to be distinguished from the dead cells (blue). The count was carried out after 24 hours, 48 hours and 72 hours of culture on contact with the hydrogel for the SW1353 and C28/I2 cell lines and for the human nasal chondrocytes (FIG. 2A to 2C).

No significant difference was observed between the number of SW1353 and C28/I2 chondrocytes and human nasal chondrocytes cultivated under the control conditions and during a culture produced on contact with the Si—HPMC hydrogel. Actinomycin D, on the other hand, caused a significant decrease in the number of cells from 24 hours onward. The number of SW1353 chondrocytes decreased by 88% and the number of C28/I2 chondrocytes decreased by 81% after 24 hours of incubation with actinomycin D. The human nasal chondrocytes decreased by 43% after 24 hours of treatment with actinomycin D.

These results revealed that the hydrogel had not modified the proliferation for the SW1353 chondrocytes, the C28/I2 chondrocytes or the human nasal chondrocytes.

Example 3

Culture of the Chondrocytes in the Hydrogel 3.1 Observation of the Chondrocytes in Three-Dimensional Culture Materials and Methods Experimental Conditions
Materials:
   Cell tracker green (CTG) (Molecular probes, Leiden, The Netherlands).
   Ethidium homodimer-1 (EthD-1) (Molecular probes).

The rabbit articular chondrocytes, the SW1353 and the C28/I2 cells, were suspended in the hydrogel in a proportion of 1 million cells/ml of hydrogel. 500 µl of this mixture were deposited in wells in 24-well culture plates. The cells were then cultivated in the presence of complete medium for 48 hours, 96 hours, 1 week and 2 weeks. At the same time, a positive cell death control was carried out by adding a solution containing 5 actinomycin D. The cells cultivated within the hydrogel were observed using the cell tracker green (CTG) and ethidium homodimer 1 (EthD-1). CTG is a colourless product which diffuses freely through cell membranes. It is then transformed in the cytoplasm by glutathione S-transferase into a fluorescent product incapable of leaving the cell. CTG produces a green fluorescence in living cells. EthD-1 is a DNA intercalating agent, the fluorescence of which increases by 40 times after binding to nucleic acids. It penetrates only those cells having membrane damage. The combined use of these two dyes allows colocalization of the living cells (green staining) and the dead cells (red staining) (Magne et al., 2003). The culture medium was drawn up and replaced by 400 µl of a 5 µM CTG solution in complete culture medium. The cells were incubated for 1 hour at 37° C. The CTG solution was then replaced by complete medium and the cells were incubated again for 30 minutes at 37° C. After rinsing with PBS, the cells were then treated for 1 hour, at ambient temperature and in the dark, with 400 µl of a 1 µM EthD-1 solution in complete medium without FCS. The medium was finally removed, the hydrogel was drawn up and placed between a slide and cover glass. The images were obtained by epifluorescent microscopy (Axioplan, Zeiss, Iena, Germany) and were recorded using a DC30 digital camera (Kappa opto-electronics Gmbh, Gleichen, Germany).

The cells in the gel were also displayed by laser scanning-inverted confocal microscopy (IFR 26, Caroline Vignes-Colombeix) after 24, 48 and 72 hours of culture as specified above. The confocal microscope produces a clear image by eliminating the signals extraneous to the focal plane. This microscope has an object stage able to move along the Z axis, allowing the focal plane to be varied and various planes of the sample thus to be displayed. The fluorescence of the CTG was traced using the fluorescein isothiocyanate detector (FITC: $\lambda$ex=488 nm; collected $\lambda$em=490 to 560 nm). The EthD-1 fluorescence was displayed by the rhodamine detector (TRITC: $\lambda$ex=568 nm, collected $\lambda$em=570 to 700 nm).

Results

In order to observe the development of the chondrocytes during a three-dimensional culture within the hydrogel, the inventors carried out staining (CTG and EthD-1) on the SW1353 and C28/I2 chondrocytes and on rabbit articular chondrocytes. They then observed the chondrocytes by fluorescent microscopy. Within the hydrogel, the SW1353 and the C28/I2 chondrocytes or the rabbit articular chondrocytes had a rounded shape and were stained markedly green by the cell tracker green. Rare cells appeared stained red. The SW1353, C28/I2 and rabbit articular chondrocytes developed three-dimensionally in the hydrogel, forming nodules, the number and the size of which increased as a function of the culture time. In order to offer a three-dimensional observation of the cells cultivated in the hydrogel, the inventors supplemented their observations by confocal microscopy. Only the observations of the C28/I2 cells are reported in this study. Confocal microscopy revealed the same results as those obtained previously with conventional fluorescent microscopy. The cells developed in the form of nodules. The cells treated for 48 hours with actinomycin D displayed marked red staining. Rare cells maintained green staining. These results indicate that, under our culture conditions, the cell tracker green/ethidium homodimer-1 double staining allowed the living cells to be distinguished from the dead cells. The observations of the SW1353 chondrocytes, the human nasal chondrocytes and the rabbit articular chondrocytes are currently being analyzed.

All of these results revealed that the SW1353 and C28/I2 chondrocytes and the rabbit articular chondrocytes maintained their viability in the three-dimensional culture within the hydrogel.

3.2. Analysis of the Chondrocyte Phenotype

In order to analyze the chondrocyte phenotype, the expression of the messengers coding for specific chondrocyte markers was investigated by RT-PCR.

(a) Experimental Conditions
Materials:
Trizol® Reagent (Invitrogen Corporation).

In order to characterize the phenotype of the cells isolated from human nasal cartilage, a fraction of the freshly isolated cells was frozen in the presence of Trizol® (pass 0, PO). The other cell fraction was distributed, in a proportion of 10,000/$cm^2$, over 25 $cm^2$ flasks. The cells were subcultured each week under the conditions described above (Chapter a)). After one, two and three passes, the cells were frozen at −80° C. in the presence of Trizol® (pass 1 (P1), 2 (P2) and 3 (P3)).

The chondrocytes freshly isolated from rabbit articular cartilage were distributed in a proportion of 1 million cells/ml of hydrogel, and 2 ml of this mixture were deposited in wells of six-well culture plates. The cells were then cultivated for 3 weeks prior to freezing in the presence of Trizol®.

(b) Extractions of the Total RNAs
Materials:
   Chloroform (VWR).
   Isopropanol (Sigma Aldrich).
   Ethanol (VWR).
   Agarose (Promega Corporation)
   Ethidium bromide (EtBr) (Promega corporation)
   Tris borate EDTA (TBE) (Invitrogen corporation)

The cells were thawed over ice and scraped: the Trizol® solution was then collected and centrifuged for 10 minutes at 12,000 rpm and at 4° C. The upper phase was removed; 200 µl of chloroform were added and the mixture was vortexed for 15 seconds. After 10 minutes of incubation at ambient temperature, the samples were centrifuged for 15 minutes at 12,000 RPM and at 4° C. The aqueous phase was removed and the total RNAs were precipitated by centrifugation (12,000 rpm, 15 minutes, 4° C.) in the presence of 500 µl of isopropanol. The supernatant was removed and the pellet was washed with 75% ethanol then dried. The total RNAs were taken up in 20 µl of water. The isolated amount of RNAs was then assessed by measuring absorbance at 260 nm. The RNA concentrations were finally adjusted to 1 µl. In order to check the integrity of the extracted RNAs, 500 ng of total RNAs were separated by electrophoresis over 1 agarose gel in a TBE buffer containing EtBr. Migration took place at 100 V for 30 minutes. The total RNAs were displayed using a UV transilluminator.

(c) Analysis of the Transcripts by RT-PCT

DNAase treatment

Materials:
Deoxyribonuclease I (DNAse I) 5 U/µl (Invitrogen Corporation)
DNAse I buffer 10× (Invitrogen Corporation)
Ethylene diamine tetra-acetic acid (EDTA) 25 mM (Invitrogen Corporation).

2 µg of RNA were removed; 1 µl of DNAse I 10× buffer and 1 µl of DNAse I (5 U/µl) were added, and the volume was adjusted to 10 µl using sterile water. The samples were then incubated for 15 minutes at ambient temperature. The reaction was stopped by adding 1 µl of 25 mM EDTA and the reaction product was placed at 65° C. for 10 minutes.

Reverse transcription (RT)

Materials:
Deoxynucleotide triphosphate (dNTP) 10 mM (Invitrogen Corporation).
0.5 µg/µl hexanucleotide primers (Random Hexamers, Promega Corporation hexaprimer C1181).
Avian Myeloblastosis Virus reverse transcriptase (AMV-RT) 10 U/µl (Promega Corporation).
AMV-RT buffer 5× (Promega Corporation)
RNAse inhibitor (RNAsin) 400 U/µl (Promega Corporation).

To each sample, previously treated with DNAase, were added 3 µl of 10 mM dNTP, 3 µl of hexanucleotide primers, 6 µl of AMV-RT buffer, 1 µl of AMV-RT and 1 µl of RNAsin; the volume was adjusted to 30 µl using sterile water. The inverse transcription was carried out using a thermocycler (Eppendorf Mastercycler, VWR) under the following conditions: 10 minutes at 25° C., 50 minutes at 42° C. and 10 minutes at 95° C. The single-strand complementary DNA solution (cDNA) thus obtained was then stored at −20° C. until it was used for the PCR reaction.

Polymerase chain reaction (PCR)

Materials:
Specific oligomer primers (MWG Biotech, Courtaboeuf, France).
Taq polymerase buffer 10× (Invitrogen Corporation).
Taq polymerase 5 U/µl (Invitrogen Corporation).
$MgCl_2$ 50 mM (Invitrogen Corporation).

The PCR was carried out using 2 µl of cDNA solution, to which were added 0.5 µl of sense primers and 0.5 µl of antisense primers at 100 ng/µl, 5 µl of Taq polymerase buffer, 1.5 µl of $MgCl_2$, 0.5 µl of Taq polymerase and 40 ml of water. The PCR reactions were carried out using a thermocycler (Eppendorf Mastercycler) under the following conditions: 3 minutes of denaturation at 94° C., followed by 30 cycles of 20 seconds at 94° C. (denaturation), 20 seconds at 60° C. (hybridization) and 20 seconds of elongation at 72° C. The PCR reaction was completed by 10 minutes of elongation at 72° C. The results of this study reveal PCR products obtained in the exponential amplification phase. The sequence of the primers, the hybridization temperatures and the size of the amplicons are specified in Table 2 (below).

TABLE 2

Sequence of the primers, hybridization temperature and size of the ampicons for the referenced genes.

| Genes | Sequences of the sense (S) and antisense (AS) primers | Tm | Size of amplicons |
|---|---|---|---|
| Human actin | S 5'-TCTCCATGTCGTCCCAGTTG-3'<br>AS 5'-AGTCTTCCCCTCCATCGTTG-3' | 60° C. | 164 pb |
| Human and rabbit collagen II (alpha 1) | S 5'-GGCAATAGCAGGTTCACGTACA-3'<br>AS 5'-GAGGCGTGAGGTCTTCTGTGA-3' | 60° C. | 108 pb |
| Human and rabbit aggrecan | S 5'-CCCTGGCAATGATGGCACTGTTC-3'<br>AS 5'-TGGCAATGATGGCACTGTTC-3' | 60° C. | 117 pb |
| Human collagen I (alpha 2) | S 5'-CATGGAAACCGTGGTCAAACT-3'<br>AS 5'-ACCAGCGATACCAGGCAGAC-3' | 60° C. | 186 pb |
| Human and rabbit collagen X | S 5'-CAAGGCACCATCTCCAGGAA-3'<br>AS 5'-GCATTTGGTATCGTTCAGCGT-3' | 60° C. | 131 pb |
| Rabbit collagen I (alpha 1) | S 5'-GATGCGTTCCAGTTCGAGTA-3'<br>AS 5'- GGTCTTCCGGTGGTCTTGTA-3' | 55° C. | 312 pb |

(d) Separation Over Agarose Gel

The PCR amplification products were electrophoretically separated over 2% agarose gel in tris borate EDTA buffer (TBE) 1×. The bands were revealed by ethidium bromide using a UV transilluminator. The size of the amplicons is indicated in Table 2.

(d) Semi-Quantitative Densitometric Analysis of the Agarose Gels

The intensity of the bands obtained over the 2% agarose gels (relevant genes and reference gene) was estimated using Leica Q500 software (Leica Imagine Systems, Cambridge, UK) allowing the semi-quantitative densitometric analysis of the amplified transcripts under various experimental conditions. The results were expressed in an arbitrary unit as the relevant gene/reference gene ratio.

Results

In order to check the maintenance of the phenotype of the rabbit articular chondrocytes in three-dimensional culture within the hydrogel, they evaluated by RT-PCR the expression of the transcripts coding for type II collagen, aggrecan and collagen X. The expression of the type I collagen was also examined at the same time.

During a monolayer culture, the inventors observed a reduction in the expression of type II collagen, aggrecan and type X collagen. After 3 weeks of culture, the type II collagen was still slightly expressed, whereas the type X collagen and aggrecan were no longer detectable. At the same time, our results revealed that the expression of type I collagen had increased after 3 weeks of monolayer culture.

Conversely, when the cells were three-dimensionally cultivated in the hydrogel for 3 weeks, the expression of type II collagen, aggrecan and type X collagen was maintained. The expression of type I collagen did not appear to be stimulated.

These results indicated that the three-dimensional culture of rabbit articular chondrocytes allows the expression of the chondrocyte markers (collagen II, aggrecan and collagen X) to be maintained.

Example 4

Study of the Redifferentiation of the Chondrocytes in Three-Dimensional Culture

In order to study the redifferentiation of the chondrocytes in three-dimensional culture in the hydrogel prepared in Example 1, freshly isolated human and rabbit nasal and articular chondrocytes were cultivated in a monolayer for 4 weeks then three-dimensionally in the hydrogel and, at the same time, in a monolayer for 4 weeks.

The total RNAs were extracted on each pass during monolayer cultures and after 2, 3 and 4 weeks for the three-dimensional cultures. The expression of type II collagen and aggrecan, specific markers of the chondrocyte phenotype, but also of type I collagen, a marker of the dedifferentiation of the chondrocytes, was examined by RT-PCR.

The results revealed that the freshly isolated chondrocytes expressed type II collagen, type I collagen and aggrecan. The expression of these markers was modified during monolayer culture; the expression of collagen II and aggrecan decreased during the various passes until it disappeared at the end of three passes, whereas the expression of type I collagen increased markedly from the first pass onward and remained markedly expressed during the various passes. The chondrocytes therefore appeared to be dedifferentiated at the end of three passes in monolayer culture. Then, during the three-dimensional culture of the chondrocytes in the hydrogel, the results revealed an increase in the expression of type II collagen and of aggrecan but also a decrease in the expression of type I collagen. These results suggested that the cells had recovered a chondrocyte phenotype in the hydrogel.

These results indicated that the hydrogel used had allowed the redifferentiation of previously dedifferentiated chondrocytes.

Statistical Tests

All the experiments were carried out in triplicate. Each experiment was carried out twice. The results were expressed as the average+/−the standard deviation. The comparative studies of the averages were carried out using the Anova test. The results were considered to be significantly different for $p<0.05$.

Example 5

Subcutaneous Implantation of Nasal Chondrocytes

Hydrogels were prepared as described in the preceding examples, integrating human chondrocytes derived from nasal cartilage (HNC). They were then implanted subcutaneously in nude mice and left for 3 weeks.

The experiments were carried out under the following five conditions:

(1) Human nasal chondrocytes three-dimensionally cultivated in the hydrogel over 15 days prior to implantation.

(2) Human nasal chondrocytes cultivated for 15 days in a monolayer prior to implantation via the hydrogel.

(3) Human nasal chondrocytes freshly isolated and implanted via the hydrogel.

(4) Human prepuce fibroblasts cultivated for 15 days in a monolayer prior to implantation via the hydrogel.

(5) Mere hydrogel.

During recovery of the implants, the inventors noted that the implants were still clearly visible 3 weeks after implantation. The hydrogel had therefore not resorbed during these 3 weeks. The histological analyses revealed the presence of positive chondrocyte nodules for the Alcian blue staining within the hydrogel, for the three conditions containing HNC (conditions 1, 2 and 3). All of these results therefore showed us that the Si—HPMC hydrogel allowed the neoformation of a cartilaginous-type tissue after 3 weeks in vivo.

BIBLIOGRAPHY

Bourges et al., 2002a, General properties of silated hydroxyethylcellulose for potential biomedical applications, Biopolymers 63(4):232-8

Bourges X, Weiss P, Daculsi G, Legeay G, 2002b Synthesis and general properties of silated-hydroxypropyl methylcellulose in prospect of biomedical use. Adv Colloid Interface Sci 99(3):215-28

Brittberg M, Lindahl A, Nilsson A, Ohlsson C, Isaksson O, Peterson L 1994 Treatment of deep cartilage defects in the knee with autologous chondrocyte transplantation. N Engl J Med 331(14):889-95

Cancedda R, Dozin B, Giannoni P, Quarto R 2003 Tissue engineering and cell therapy of cartilage and bone. Matrix Biol 22(1):81-91

Ghayor C, Herrouin J F, Chadjichristos C, Ala-Kokko L, Takigawa M, Pujol J P, Galera P 2000 Regulation of human COL2A1 gene expression in chondrocytes. Identification of C-Krox-responsive elements and modulation by phenotype alteration. J Biol Chem 275(35):27421-38

Goldring M B, Birkhead J R, Suen L F, Yamin R, Mizuno S, Glowacki J, Arbiser J L, Apperley J F 1994 Interleukin-1 beta-modulated gene expression in immortalized human chondrocytes. J Clin Invest 94(6):2307-16

Hunziker E B 2002 Articular cartilage repair: basic science and clinical progress. A review of the current status and prospects. Osteoarthritis Cartilage 10(6):432-63

Magne D, Bluteau G, Faucheux C, Palmer G, Vignes-Colombeix C, Pilet P, Rouillon T, Caverzasio J, Weiss P, Daculsi G, Guicheux J 2003 Phosphate is a specific signal for ATDC5 chondrocyte maturation and apoptosis-associated mineralization: possible implication of apoptosis in the regulation of endochondral ossification. J Bone Miner Res 18(8): 1430-42

Mengshol J A, Vincenti M P, Coon C I, Barchowsky A, Brinckerhoff C E 2000 Interleukin-1 induction of collagenase 3 (matrix metalloproteinase 13) gene expression in chondrocytes requires p38, c-Jun N-terminal kinase, and nuclear factor kappaB: differential regulation of collagenase 1 and collagenase 3. Arthritis Rheum 43(4):801-11

Shapiro F, Koide S, Glimcher M J 1993 Cell origin and differentiation in the repair of full-thickness defects of articular cartilage. J Bone Joint Surg Am 75(4):532-53

What is claimed is:

1. A method for the three-dimensional ex vivo culture of chondrocytes in a silanized hydrogel, comprising the steps of:
   (a) reacting hydroxypropylmethylcellulose (HPMC) with a compound of formula (I):

$$XSi(OZ)_3 \quad (I)$$

wherein X represents a halogen atom or a hydrocarbon group having an epoxy function, and Z is selected from the group consisting of a hydrogen atom, an alkali metal, and an alkyl group, and wherein the resultant silanized hydrogel from the reaction self-crosslinks as a function of pH;
   (b) contacting chondrocytes with the silanized hydrogel; and
   (c) culturing the chondrocytes in the hydrogel ex vivo.

2. The method as claimed in claim 1, wherein the silanized HPMC carries silanolate side groups representing from 0.5 to 5% of the total dry weight of the HPMC.

3. The method as claimed in claim 1, wherein the silanized HPMC has the formula:

(HPMC)—O—CH$_2$—CH—OH—CH$_2$O—(CH$_2$)$_3$—Si—(O$^-$Na$^+$)$_3$.

4. The method as claimed in claim 1, wherein the hydrocarbon group is C$_{2-20}$.

5. The method as claimed in claim 1, wherein the alkyl group is C$_{1-5}$.

6. An ex vivo process for the preparation of a complex of cells integrated in a silanized hydrogel, the complex being intended to be injected into a cartilaginous site, wherein said process comprises the steps of
  (a) reacting hydroxypropylmethylcellulose (HPMC) with a compound of formula (I):

XSi(OZ)$_3$  (I)

wherein X represents a halogen atom or a hydrocarbon group having an epoxy function and Z is selected from the group consisting of a hydrogen atom, an alkali metal, and an alkyl group, and wherein the resultant silanized hydrogel from the reaction self-crosslinks as a function of pH;
  (b) mixing the silanized hydrogel of step (a) with a biological buffer;
  (c) ex vivo mixing of chondrocytes with the silanized hydrogel of step (b) to produce a mixture; and
  (d) crosslinking the silanized hydrogel in the mixture at an appropriate pH for said crosslinking under appropriate conditions and time for the integration to result in a three-dimensional culture of the chondrocytes in the silanized hydrogel.

7. The process as claimed in claim 6, including the following ex vivo steps:
  monolayer amplification of chondrocytes on a solid support;
  harvesting of the amplified chondrocytes, dedifferentiated through the monolayer amplification thereof;
  mixing of the dedifferentiated amplified chondrocytes with the hydrogel in a biological buffer at an appropriate pH for the crosslinking of the hydrogel, resulting in the integration of the chondrocytes within the hydrogel and in the redifferentiation thereof.

8. The process as claimed in claim 6, wherein the silanized HPMC carries silanolate side groups representing from 0.5 to 5% of the total dry weight of the HPMC.

9. The process as claimed in claim 6, wherein the silanized HPMC has the formula:

(HPMC)—O—CH$_2$—CH—OH—CH$_2$O—(CH$_2$)$_3$—Si—(O$^-$Na$^+$)$_3$.

10. The method as claimed in claim 6, wherein the hydrocarbon group is C$_{2-20}$.

11. The method as claimed in claim 6, wherein the alkyl group is C$_{1-5}$.

12. An ex vivo process for the preparation of a complex of cells integrated in a silanized hydrogel, the complex being intended to be injected into a cartilaginous site, wherein said process comprises the steps of:
  (a) reacting, hydroxypropylmethylcellulose HPMC with a compound of formula (I):

XSi(OZ)$_3$  (I)

wherein X represents a halogen atom or a hydrocarbon group having an epoxy function, and Z is selected from the group consisting of a hydrogen atom, an alkali metal, and an alkyl group, and wherein the resultant silanized hydrogel from the reaction self-crosslinks as a function of pH;
  (b) mixing the silanized hydrogel of step (a) with biological buffer;
  (c) ex vivo mixing of undifferentiated cells capable of chondrogenic differentiation with the silanized hydrogel of step (b) to produce a mixture; and
  (d) crosslinking the silanized hydrogel at an appropriate pH for said crosslinking under appropriate conditions and time for the integration to result in a three-dimensional culture of the chondrocytes derived from the differentiation of said undifferentiated cells in the silanized hydrogel.

13. The process as claimed in claim 12, wherein the HPMC carries silanolate side groups representing from 0.5 to 5% of the total dry weight of the HPMC.

14. The process as claimed in claim 12, wherein the silanized HPMC has the formula:

(HPMC)—O—CH$_2$—CH—OH—CH$_2$O—(CH$_2$)$_3$—Si—(O$^-$Na$^+$)$_3$.

15. The method as claimed in claim 12, wherein the hydrocarbon group is C$_{2-20}$.

16. The method as claimed in claim 12, wherein the alkyl group is C$_{1-5}$.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
tctcctagtc gtcccagttg                                                   20

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
agtcttcccc tccatcgttg                                                   20

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
ggcaatagca ggttcacgta                                                   20

<210> SEQ ID NO 4
<211> LENGTH: 21
<212> TYPE: DNA
<213> ORGANISM: Artificial sequence
<220> FEATURE:
<223> OTHER INFORMATION: primer

<400> SEQUENCE: 4
gaggcgtgag gtcttctgtg a                                                 21

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5
ccctggcaat gatggcactg ttc                                               23

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
tggcaatgat ggcactgttc                                                   20

<210> SEQ ID NO 7
<211> LENGTH: 21
<212> TYPE: DNA

```
<213> ORGANISM: Artificial sequence
<220> FEATURE:
<223> OTHER INFORMATION: primer

<400> SEQUENCE: 7
catggaaacc gtggtcaaac t                                              21

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
accagcgata ccaggcagac                                                20

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9
caaggcacca tctccaggaa                                                20

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
gcatttggta tcgttcagcg t                                              21

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
gatgcgttcc agttcgagta                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ggtcttccgg tggtcttgta                                                20
```